(12) United States Patent
Grant

(10) Patent No.: US 11,998,444 B2
(45) Date of Patent: *Jun. 4, 2024

(54) INTRAOCULAR LENS HAVING INPUT AND OUTPUT ELECTRONICS

(71) Applicant: Crown Holdings, LLC, Newport Beach, CA (US)

(72) Inventor: Robert Edward Grant, Laguna Beach, CA (US)

(73) Assignee: CROWN HOLDINGS, LLC, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,284

(22) Filed: Dec. 16, 2022

(65) Prior Publication Data
US 2023/0404741 A1    Dec. 21, 2023

Related U.S. Application Data

(63) Continuation of application No. 16/422,747, filed on May 24, 2019, now Pat. No. 11,559,391, which is a
(Continued)

(51) Int. Cl.
*A61F 2/16* (2006.01)
*A61B 5/00* (2006.01)
(Continued)

(52) U.S. Cl.
CPC .......... *A61F 2/1624* (2013.01); *A61B 5/0031* (2013.01); *A61B 5/1112* (2013.01);
(Continued)

(58) Field of Classification Search
CPC .... A61F 2/1613; A61F 2/1624; A61F 2/1648; A61F 2002/1681; A61F 2002/1689;
(Continued)

(56) References Cited

U.S. PATENT DOCUMENTS 5,275,623 A    1/1994 Sarfarazi
5,682,210 A    10/1997 Weirich
(Continued)

FOREIGN PATENT DOCUMENTS

WO    WO 2006-015315 A2    2/2006
WO    WO-2011163080 A1 *  12/2011 ........... A61F 2/1624

OTHER PUBLICATIONS

Ghent University, "Breakthrough in augmented reality contact lens," ScienceDaily, Dec. 5, 2012; in 4 pages.
(Continued)

*Primary Examiner* — Javier G Blanco
(74) *Attorney, Agent, or Firm* — Knobbe, Martens, Olson & Bear, LLP

(57) ABSTRACT

Systems and methods involving an intraocular implant with input and/or output electronics are described. In some embodiments, the system includes an intraocular lens having at least one optic operably coupled to a haptic, one or more input electronics on the haptic and/or the optic; and one or more output electronics on the haptic and/or the optic for receiving and/or transmitting data.

14 Claims, 4 Drawing Sheets

Related U.S. Application Data continuation of application No. 15/593,200, filed on May 11, 2017, now Pat. No. 10,299,912, which is a continuation of application No. 14/553,900, filed on Nov. 25, 2014, now Pat. No. 9,662,199.

(60) Provisional application No. 61/909,257, filed on Nov. 26, 2013.

(51) Int. Cl.
 *A61B 5/11* (2006.01)
 *A61F 2/14* (2006.01)

(52) U.S. Cl.
 CPC ............ *A61B 5/686* (2013.01); *A61B 5/7445* (2013.01); *A61F 2/14* (2013.01); *A61B 2560/0209* (2013.01); *A61B 2560/0214* (2013.01); *A61B 2560/0219* (2013.01); *A61B 2560/0487* (2013.01); *A61F 2002/1699* (2015.04); *A61F 2250/0002* (2013.01)

(58) Field of Classification Search
 CPC ..... A61F 2250/0002; A61F 2250/0001; A61B 5/7445; A61B 5/0031
 See application file for complete search history.

(56) References Cited

U.S. PATENT DOCUMENTS

| | | |
|---|---|---|
| 6,443,893 B1 | 9/2002 | Schnakenberg et al. |
| 7,001,427 B2 | 2/2006 | Aharoni et al. |
| 7,542,210 B2 | 6/2009 | Chirieleison, Sr. |
| 7,572,011 B2 | 8/2009 | Pollard et al. |
| 8,060,560 B2 | 11/2011 | Vonog et al. |
| 8,062,129 B2 | 11/2011 | Pope et al. |
| 8,096,654 B2 | 1/2012 | Amirparviz et al. |
| 8,171,154 B2 | 5/2012 | Vonog et al. |
| 8,446,341 B2 | 5/2013 | Amirparviz et al. |
| 8,545,555 B2 | 10/2013 | Berge |
| 8,834,566 B1 | 9/2014 | Jones |
| 9,662,199 B2 | 5/2017 | Grant |
| 9,999,497 B2 | 6/2018 | Shiuey |
| 10,299,912 B2 | 5/2019 | Grant |
| 2004/0181279 A1 | 9/2004 | Nun |
| 2005/0131535 A1 | 6/2005 | Woods |
| 2008/0086206 A1 | 4/2008 | Nasiatka et al. |
| 2008/0161915 A1 | 7/2008 | Ren |
| 2009/0189974 A1* | 7/2009 | Deering ............ G02B 27/0093 348/51 |
| 2009/0279050 A1 | 11/2009 | McGinn et al. |
| 2010/0103368 A1* | 4/2010 | Amirparviz ............. G02C 7/04 977/920 |
| 2012/0296426 A1 | 11/2012 | Brady et al. |
| 2013/0044042 A1 | 2/2013 | Olsson et al. |
| 2013/0090534 A1 | 4/2013 | Burns et al. |
| 2013/0194540 A1 | 8/2013 | Pugh et al. |
| 2013/0282117 A1 | 10/2013 | Van Heugten et al. |
| 2014/0240656 A1 | 8/2014 | Pugh |
| 2015/0182330 A1 | 7/2015 | Grant |
| 2015/0216652 A1 | 8/2015 | Jansen |
| 2015/0301338 A1 | 10/2015 | Van Heugten |
| 2016/0070038 A1 | 3/2016 | Peyman |

OTHER PUBLICATIONS

Lingley et al., "A single-pixel wireless contact lens display", Journal of Micromechanics and Microengineering, 2011, vol. 21, Article Np.: 125014 (internal pp. 1-15) See abstract: pp. 1-13; figures 1, 6, 7.

Leonardi, Matteo, et al. "First steps toward noninvasive intraocular pressure monitoring with a sensing contact lens." Investigative ophthalmology & visual science 45.9 (2004):3113-3117.

Pandey, J. et al., "A Fully Integrated RF-Powered Contact Lens With a Single Element Display", IEEE Transactions on Biomedical Circuits and Systems, 2010, vol. 4, pp. 454-461, See Abstract: pp. 454-460; figures 1-14.

Search Report and Written Opinion in PCT/US2014/067768 in 12 pages dated Feb. 13, 2015.

Stiles et al., "An Intraocular Camera for Retinal Prosthesis: Restoring Sight to the Blind," World Scientific, 2010; in 2 pages.

Notice of Allowance dated Mar. 15, 2017 in U.S. Appl. No. 14/553,900 in 8 pages.

Zhou et al., "In vivo Evaluation of Implantable Micro-Camera for Visual Prosthesis," Investigative Ophthalmology & Visual Science, vol. 48, Issue 13, May 2007; in 2 pages.

\* cited by examiner

INTRAOCULAR LENS HAVING INPUT AND OUTPUT ELECTRONICS

RELATED APPLICATIONS

This application claims the benefit as a continuation of U.S. application Ser. No. 16/422,747 filed on May 24, 2019, which in turn claims the benefit as a continuation of U.S. application Ser. No. 15/593,200 filed on May 11, 2017, which in turn claims the benefit as a continuation of U.S. application Ser. No. 14/553,900 filed on Nov. 25, 2014, which in turn claims the benefit under 35 U.S.C. § 119(e) as a nonprovisional application of U.S. Prov. Pat. App. No. 61/909,257 filed on Nov. 26, 2013. Each of the foregoing priority applications are hereby incorporated by reference in their entireties.

BACKGROUND

Field of the Invention

The invention is directed, in some aspects, to a device implantable in or on the body, such as an intraocular device that includes one or more input or output electronics.

Description of the Related Art

External wearable devices are known such as Google Glass®, which include a computing system, camera, and a display, such as described in U.S. Pub. No. 2013/0044042 A1. Also known in the art are sensing contact lenses capable of noninvasively measuring intraocular pressure, such as described in Leonardi et al., Inv. Opthal. Vis. Sci. September 2004, vol. 45 No. 9; as well as intraocular physiologic sensors, as described in U.S. Pub. No. 2013/0090534 A1. All of the references disclosed herein are hereby incorporated by reference in their entireties.

What is needed is a convenient, long-term implant, such as an intraocular lens, that is comfortable and not noticeable to the patient after implantation, not externally visible and thus private, and that is configurable with any number of input and output electronics, such as displays, cameras, GPS, RFID, and the like, for a wide variety of indications, including facilitating health, safety, knowledge, and communication, for example.

SUMMARY

Disclosed herein is an implantable intraocular lens, including an optic; a haptic operably connected to the optic; a camera operably attached to the haptic; a power source operably attached to the haptic; a display on the optic; and a communications module configured to wirelessly transmit and receive information with respect to an external device. The lens could be, in some cases, a pseudophakic lens, an accommodating lens, or a phakic lens. In some embodiments, the lens could include a plurality of optics. The camera could include a video camera. The display could include LED, OLED, or other technology. The display could be centered on the optic, or off-center on the optic. The system could also include, for example, tracking elements, such as a GPS chip and/or RFID chip. The communications module could include any appropriate technology based upon the desired clinical result, such as cellular of 802.11 technology. The power source can be wirelessly rechargeable via an external source in some cases.

DETAILED DESCRIPTION

Figure 1:
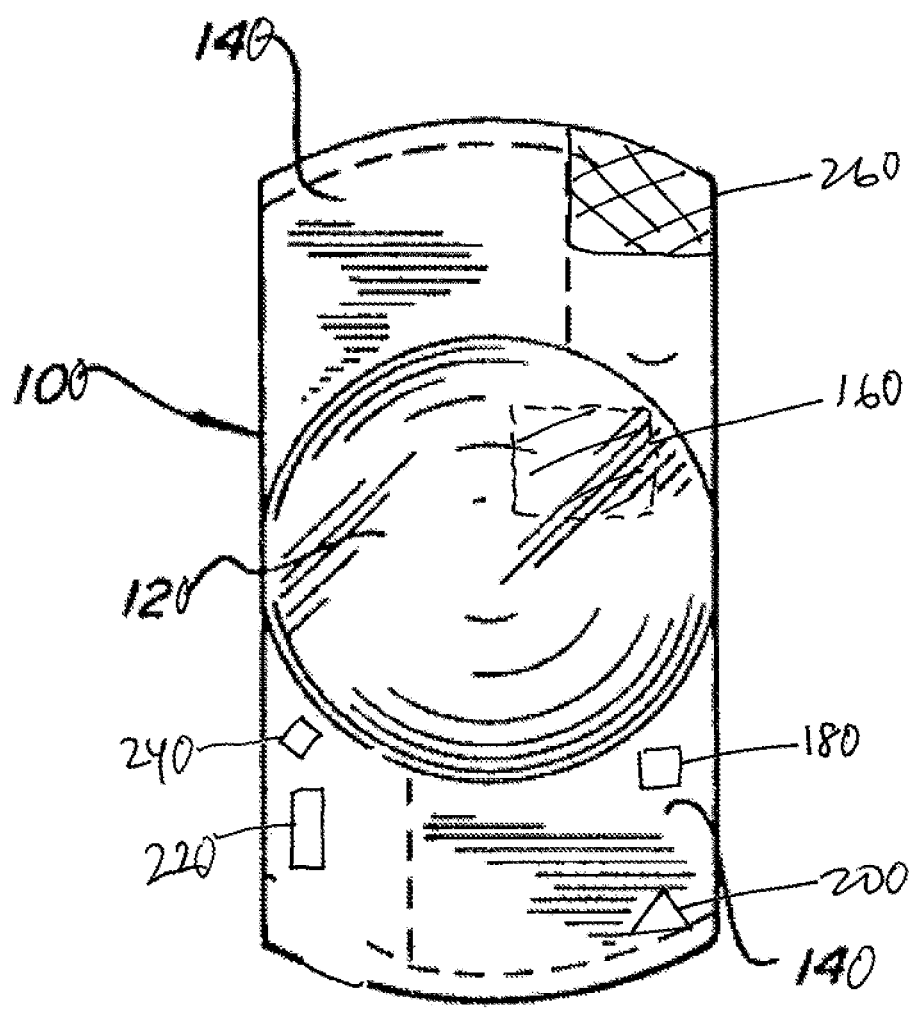
FIG. 1 is a schematic illustrating an intraocular lens with various input and output electronics thereon, according to some embodiments of the invention.

Systems and methods involving an intraocular implant with input and/or output electronics will now be described. In some embodiments, the system includes an intraocular lens having at least one optic operably coupled to a haptic, one or more input electronics on the haptic and/or the optic; and one or more output electronics on the haptic and/or the optic for receiving and/or transmitting data. FIG. 1 schematically illustrates an intraocular lens 10 having an optic 12 and a haptic 14 operably connected to the optic 12. Shown is a display 16 on the optic, configured to display an image to the patient. Shown on the haptic 14 is a camera 18, processor 20, communications module 22 (e.g., transmitting and/or receiving antennas), and sensors, e.g., location module (e.g., a GPS) 24, all with a wired or wireless connection to one or more power source(s) 26.

Further non-limiting possible features that can be used or modified for use with the system and method are described below.

Input and Output Electronics

As noted above, FIG. 1 illustrates an example system 100 for receiving, transmitting, and displaying data. The system 100 is shown in the form of an intraocular implant, such as an implantable intraocular lens. While FIG. 1 illustrates an intraocular lens as an example of an implantable computing device, other types of intraocular implants could additionally or alternatively be used. In some embodiments, the implant need not necessarily be intraocular, and instead be at another anatomic location, such as, for example, the back of the head which is not in a person's normal field of vision if looking straight ahead, or attached to an extremity, for example.

As illustrated in FIG. 1 above, the intraocular lens includes an optic component and a haptic component. All or part of the haptic may be formed of a solid biocompatible structure of plastic and/or metal, or may be formed of a hollow structure of similar material so as to allow wiring and component interconnects to be internally routed through the haptic. Other materials may be possible as well.

The one or more optics, or display section on the optic may be formed of any material that can suitably display a projected image or graphic. The optic can be preferably sufficiently transparent to allow a user to see through the optic. Combining these two features of the optic may facilitate an augmented reality or heads-up display where the projected image or graphic is superimposed over a real-world view as perceived by the user through the lens.

As noted above in reference to FIG. 1, the system 100 may also include an on-board computing system 200, a still or video camera 180, and/or a sensor 240. The on-board computing system 200 is shown to be positioned on the haptic 140, such as a distal or posterior portion of the haptic 140, for example; however, the on-board computing system 200 may be provided on other parts of the haptic 140 or may be positioned remote from the intraocular implant 100 (e.g., the on-board computing system 200 could be implanted in another anatomic location inside or outside of the orbit, or even be external to the body, wire- or wirelessly-connected to the intraocular implant 100). The on-board computing system 200 may include a processor and memory, for example, and graphics, motion, or other co-processors, for example. The on-board computing system 200 may be configured to receive and analyze data from the video camera 180 (and possibly from other sensory devices, user interfaces, or both) and generate images for output on the optic 120.

The video camera 180 is shown positioned on the haptic 140; however, the video camera 180 may be provided on other parts of the intraocular device 102. The video camera 180 may be configured to capture images at various resolutions or at different frame rates. Many video cameras with a small form-factor, such as those used in cell phones or webcams, for example, may be incorporated into an example of the system 100.

Further, although FIG. 1 illustrates one video camera 180, more video cameras may be used, and each may be configured to capture the same view, or to capture different views. For example, the video camera 180 may be forward facing to capture at least a portion of the real-world view perceived by the user. This forward facing image captured by the video camera 180 may then be used to generate an augmented reality where computer generated images appear to interact with the real-world view perceived by the user. In some embodiments, the video camera could be configured for night vision, to detect infrared, x-rays, or other forms of radiation that may or may not be normally visible to the human eyes. In some embodiments, this may be advantageous for medical, security, or military applications, for example. The video can also be transmitted and streamed to and/or saved to a storage medium on an external device. In some embodiments, the system could also include an audio-capture element, such as one or more microphones for example to capture audio input.

The one, two, or more sensors 240 are shown on the haptic 120 portion of the device 100; however, the sensor 240 may be positioned on other parts of the intraocular device 100. The sensor 240 may include one or more of a gyroscope, an accelerometer, GPS, RFID, physiologic sensors, piezo-electric crystal sensors, and the like, for example. Other sensing devices may be included within, or in addition to, the sensor 240 or other sensing functions may be performed by the sensor 240. The GPS locator and/or RFID or other device could allow, for example, a third-party healthcare provider or emergency responder to locate the patient with the implanted lens in the event of a medical emergency communicated to such provider or responder from the lens via wireless technology on the lens itself and/or an external device, such as a laptop computer, smartphone or smart watch.

In some embodiments, the optic may act as a display element. The intraocular device may include a first projector coupled to a surface of the haptic and configured to project a display 160 onto a surface of the optic 120. In some embodiments, instead of or in addition to a display, an optically clear aperture can be present with an optical spherical power.

In alternative embodiments, other types of display elements may also be used. For example, the optic(s) 120 themselves may include: a transparent or semi-transparent matrix display, such as an electroluminescent display or a liquid crystal display, one or more waveguides for delivering an image, or other optical elements capable of delivering an in focus image to the user. A corresponding display driver may be disposed within the haptic 140 for driving such a matrix display. Alternatively or additionally, a laser or LED source and scanning system could be used to draw a raster display directly onto the retina of one or more of the user's eyes. Other possibilities exist as well.

In some embodiments, an intraocular computing device may include a single display which may be coupled to the device. The display may be formed on one of the optics of the intraocular computing device, such as a lens element described herein, and may be configured to overlay computer-generated graphics in the user's view of the physical world. The display can be provided in a center of a lens of the implantable device, however, the display may be provided in other positions, such as medially or laterally, and/or anteriorly or posteriorly offset. The display can be controllable via the computing system that is coupled to the display via, for example, an optical waveguide.

Figure 2:
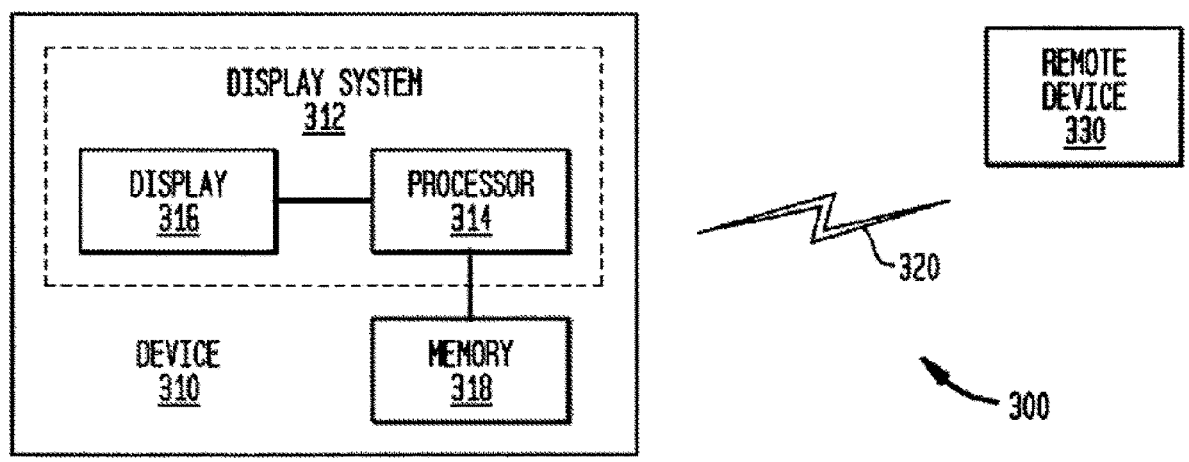
FIG. 2 illustrates an embodiment of a system for receiving, transmitting, and displaying data, according to some embodiments of the invention.

FIG. 2 illustrates a schematic drawing of an example computer network infrastructure. In system 300, a device 310 communicates using a communication link 320 (e.g., a wired or wireless connection) to a remote device 330. The device 310 may be any type of device that can receive data and display information corresponding to or associated with the data. For example, the device 310 may be a heads-up display system, or any of the implantable devices described with reference elsewhere herein.

Thus, the device 310 may include a display system 312 comprising a processor 314 and a display 316. The display 310 may be, for example, an optical see-through display, an optical see-around display, or a video see-through display. The processor 314 may receive data from the remote device 330, and configure the data for display on the display 316. The processor 314 may be any type of processor, such as a micro-processor or a digital signal processor, for example.

The device 310 may further include on-board data storage, such as memory 318 coupled to the processor 314. The memory 318 may store software that can be accessed and executed by the processor 314, for example.

The remote device 330 may be any type of computing device or transmitter including a desktop or laptop computer, a mobile telephone, tablet computing device, smartwatch, etc., that is configured to transmit data to the device 310. The remote device 330 and the device 310 may contain hardware to enable the communication link 320, such as processors, transmitters, receivers, antennas, etc.

In FIG. 2, the communication link 320 is illustrated as a wireless connection; however, wired connections may also be used. For example, the communication link 320 may be a wired serial bus such as a universal serial bus or a parallel bus. A wired connection may be a proprietary connection as well. The communication link 320 may also be a wireless connection using, e.g., Bluetooth® radio technology, communication protocols described in IEEE 802.11 (including any IEEE 802.11 revisions), Cellular technology (such as GSM, CDMA, UMTS, EVDO, WiMAX, or LTE), or Zigbee® technology, among other possibilities. The remote device 330 may be accessible via the Internet and may include a computing cluster associated with a particular web service (e.g., social-networking, photo sharing, address book, etc.).

In some embodiments, if intraocular implants with electronics as described herein, such as IOLs, are implanted bilaterally, the electronics can be configured such that both eyes see the same image display, or different image displays.

In some embodiments, the electronics can respond to input, such as the amount of light that reaches the camera or sensor proximate the lens for example. For example, if a patient closes their eyes for a predetermined period of time, for example, this could trigger a lock or sleep feature, e.g., via a light sensor detecting a lack of light, allowing a user to toggle the power for device 10 between on and off states. In other embodiments, a pressure sensor on the device could detect, for example, a patient applying manual pressure over one or both eyes, using their hands, for example, which could toggle the power for the device or activate or deactivate some or all of the electronics.

Additional input structures can be included in the device. These can include a camera and one, two, or more sensors. The camera can be used to take pictures or record a video at the user's discretion. The camera can also be used by the device to obtain an image of the user's view of his or her environment to use in implementing augmented reality functionality. The sensor can be, for example a light sensor that can be used by firmware or software associated with the camera. The camera and sensor can be included in a housing positioned, for example, about the haptic. Other locations for the camera and sensor are also possible.

Power Supply

The device can contain electronic circuitry and/or a power source, such as a battery for device. This circuitry can include controls for the display, the camera, the sensor, or other features. Additionally the housing can include memory, a microprocessor or communications devices, such as cellular, short-range wireless (e.g. Bluetooth), or WiFi circuitry for connection to a remote device. The battery can, for example, be a rechargeable battery such as a lithium-ion or nickel-cadmium battery and can be removable or can be permanent or semi-permanent.

In some embodiments, some or all of the electronic components of the implantable device are wholly or partially powered using a power source that can convert material found in the human body into, for example, electrical power. For example, in some embodiments, the power source is an electrochemical fuel cell that produces electricity using glucose dissolved in blood, aqueous humor, or other body fluids. Thus, the glucose itself acts as a renewable fuel for powering the electronics. In contrast, other electronics may be wholly dependent upon batteries or an external source for their power. Alternatively, some implantable electronics rely upon external devices for power (e.g., for real-time operation using the externally-supplied power or to re-charge an internal battery). For example, electronics may be externally powered via inductive coupling or RF energy from an external device.

Additional components can be included in device, such as additional inputs, control circuitry boards, antennae or the like. The various locations in which these additional components are affixed to the haptic can also be selected to allow for a predetermined weight distribution.

While various embodiments illustrating computing systems and components are described herein, it is recognized that the functionality provided for in the components and modules of computing system may be combined into fewer components and modules or further separated into additional components and modules. Modules can include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Any modules can be executed by one or more CPUs.

A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage. In addition, all the methods described herein may be executed as instructions on a CPU, and may result in the manipulation or transformation of data.

In some embodiments, hardware components of the system includes a CPU, which may include one, two, or more microprocessors. The system further includes a memory, such as random access memory ("RAM") for temporary storage of information and a read only memory ("ROM") for permanent storage of information, and a mass storage device, such as a hard drive, flash drive, diskette, or optical media storage device, which can be external to the body in some cases.

Intraocular Implant

In some embodiments, as discussed above, an implantable intraocular device includes an intraocular lens. An intraocular lens can include one, two, or more optic components and haptic components. The intraocular lens could be, for example, a phakic or pseudophakic intraocular lens. A pseudophakic IOL could be desirable in a patient having a cataract for example, and could be a conventional or accommodating IOL in some embodiments. Various non-limiting examples of some embodiments of lens features, such as optics and haptics, that can be used with systems and methods of intraocular lens are described below.

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange. In some cases, a phakic IOL, or PIOL can be inserted. A PIOL is a special kind of intraocular lens that is implanted surgically into the eye to correct myopia (nearsightedness). They are called "phakic" because the eye's natural lens is left untouched. This is in contrast to intraocular lenses that are implanted into eyes after the eye's natural lens has been removed during cataract surgery.

The simplest IOLs have a single focal length, or, equivalently, a single power. Unlike the eye's natural lens, which can adjust its focal length within a particular range in a process known as accommodation, these single focal length IOLs cannot accommodate. As a result, objects at a particular position away from the eye appear in focus, while objects at an increasing distance away from that position appear increasingly blurred.

In some embodiments, an IOL is configured to zoom in and/or out, such as on far-away objects for long distance viewing, through a liquid crystal lens array or other means. In some embodiments, the lens can be configured for presbyopic correction (e.g., both multifocal and small aperture correction).

An improvement over the single focal length IOLs is an accommodating IOL, which can adjust its power within a particular range. Some examples of accommodating IOLs are described in U.S. Pub. No. 2012/0296426 A1 to Brady et al., which is incorporated by reference in its entirety. With accommodating IOLs, the patient can clearly focus on objects in a range of distances away from the eye, rather than at a single distance. This ability to accommodate is of benefit for some patients, and can potentially more closely approximates the patient's natural vision than a single focal length IOL in some cases.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accommodation range itself is defined as the near power minus the far power. In general, an accommodation range of 4 diopters is considered sufficient for most patients.

The human eye contains a structure known as the capsular bag, which surrounds the natural lens. The capsular bag is transparent, and serves to hold the lens. In the natural eye, accommodation is initiated by a series of zonular fibers, also known as zonules. The zonules are located in a relatively thick band mostly around the equator of the lens, and impart a largely radial force to the capsular bag that can alter the shape and/or the location of the natural lens and thereby change its power.

In a typical surgery in which the natural lens is removed from the eye, the lens material is typically broken up and vacuumed out of the eye, but the capsular bag is left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which refracts light that passes through it and forms an image on the retina, and a haptic, which is a structure that mechanically couples the optic to the capsular bag. During accommodation, the zonules exert a force on the capsular bag, which in turn exerts a force on the optic. The force may be transmitted from the capsular bag directly to the optic, or from the capsular bag through the haptic to the optic.

A desirable optic, in some cases, for an accommodating IOL is one that distorts in response to a squeezing or expanding radial force applied to the equator of the optic (e.g., by pushing or pulling on the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

The optic can be coupled with a suitable haptic to couple the optic to the capsular bag. The haptic can permit diametric (or, equivalently, radial) motion of the optic by coupling the force exerted by the capsular bag to the edge of the optic. Some other haptic designs are disclosed, for example, in U.S. Pat. Pub. No. 2005/0131535 to Woods, which is hereby incorporated by reference in its entirety. Haptic designs can also be used with other IOL styles. U.S. Pat. No. 5,275,623 to Sarfarazi, which is incorporated by reference in its entirety, discloses a lens that uses a pair of optics and a flexible haptic that responds to the forces of the capsular bag by changing the separation between the optics. As yet another example, U.S. Pat. Pub. No. 2004/0181279 to Nun, which is hereby incorporated by reference in its entirety, discloses a lens that has an optic located between a rigid haptic and the posterior wall of the capsular bag. Accordingly, in some cases there exists a need for an intraocular lens with a haptic that permits diametric motion of the optic by efficiently coupling the force exerted by the capsular bag and zonules to the edge of the optic. Such a haptic would enable use of a desirable style of optic, which changes its power (e.g., radius of curvature, shape and/or thickness) in response to a squeezing or expanding force applied radially to its edge.

In a healthy human eye, the natural lens is housed in a structure known as the capsular bag. The capsular bag is driven by zonular fibers (also known as zonules) in the eye, which can compress and/or pull on the capsular bag to change its shape. The motions of the capsular bag distort the natural lens in order to change its power and/or the location of the image, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the zonules, it is desirable that the implanted intraocular lens change its power and/or the location of the image in a manner similar to that of the natural lens. Such an accommodating lens may produce vastly improved vision over a lens with a fixed power and location that does not accommodate.

Figure 3:
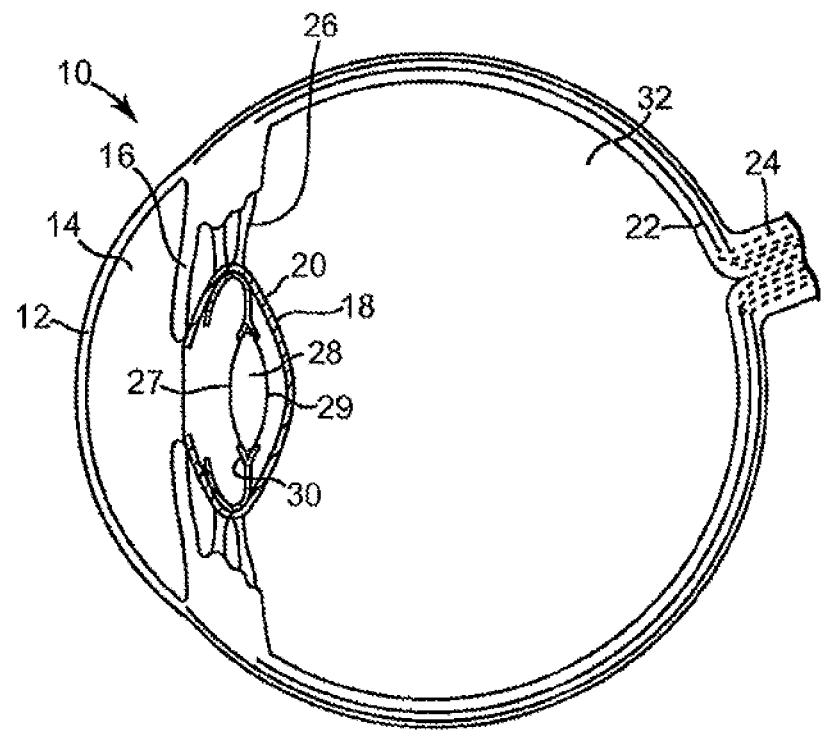
FIG. 3 is a plan drawing of a human eye having an implanted intraocular lens in an accommodative "near" state, that can have electronics or other features as disclosed herein according to some embodiments of the invention.

FIG. 3 shows a human eye 10, after an accommodating intraocular lens according to embodiments of the present invention has been implanted. Light enters from the left of FIG. 3, and passes through the cornea 12, the anterior chamber 14, the iris 16, and enters the capsular bag 18. Prior to surgery, the natural lens occupied essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

A well-corrected eye forms an image at the retina 22. If the lens has too much or too little power, the image shifts axially along the optical axis away from the retina, toward or away from the lens. Note that the power required to focus on a close or near object is more than the power required to focus on a distant or far object. The difference between the "near" and "far" powers is known typically as the range of accommodation. A normal range of accommodation is about 4 diopters, which is considered sufficient for most patients, although as low as 1 or 2 diopters may be acceptable, and in some instances between about 4 diopters and about 10 diopters or more may be useful. Embodiments of the present invention may produce accommodation within this entire range, or as low as 1 diopter, with a preferable range of accommodation between about 2 diopters and about 6 diopters, and more preferably about 4 diopters (for example, 3-5 diopters, 3.5-4.5 diopters, and so forth) of accommodation under normal zonular forces.

The capsular bag is acted upon by the zonules 26, which distort the capsular bag 18 by compressing and/or stretching it radially in a relatively thick band about its equator. Experimentally, it is found that the zonules typically exert a total force of up to about 10 grams of force, often in the range of between about 6 and about 9 grams of force, which is distributed typically generally uniformly around the equator of the capsular bag 18. Although the range of zonule force may vary from patient to patient, it should be noted that for each patient, the range of accommodation is limited by the total force that the zonules 26 can exert. Therefore, it is highly desirable that the intraocular lens be configured to vary its power over the full range of accommodation, in response to this limited range of forces exerted by the zonules.

Because the zonules' force is limited, it is desirable to use a fairly thin lens, compared to the full thickness of the capsular bag. In general, a thin lens can distort more easily than a very thick one, and may therefore convert the zonules force more efficiently into a change in power. In other words, for a relatively thin lens, a lower force is required to cover the full range of accommodation.

Note that there is an optimum thickness for the lens, which depends on the diameter of the optic. If the lens is thinner than this optimum thickness, the axial stiffness becomes too high and the lens changes power less efficiently. In other words, if the edge thickness is decreased below its optimal value, the amount of diopter power change for a given force is decreased. For instance, for an optic having a diameter of 4.5 mm, an ideal edge thickness may be about 1.9 mm, with edge thicknesses between about 1.4 mm and about 2.4 having acceptable performance as well. Alternately, optic diameters may be in a range between about 4 mm and about 8 mm, and edge thicknesses may be in a range above about 0.2 mm.

Note that the lens may be designed so that its relaxed state is the "far" condition (sometimes referred to as "disaccommodative biased"), the "near" condition ("accommodative biased"), or some condition in between the two ("intermediate biased").

The intraocular lens itself has two components: an optic 28, which is made of a transparent, deformable and/or elastic material, and a haptic 30, which holds the optic 28 in place and mechanically transfers forces on the capsular bag 18 to the optic 28. The haptic 30 may have an engagement member with a central recess that is sized to receive the peripheral edge of the optic 28.

When the eye 10 is focused on a relatively close object, as shown in FIG. 3, the zonules 26 compress the capsular bag 18 in a relatively thick band about its equator. The capsular bag 18 changes shape, becoming thicker at its center and having more steeply curved sides. As a result of this action, the power of the lens increases (e.g., one or both of the radii of curvature can decrease, and/or the lens can become thicker, and/or the lens may also move axially), placing the image of the relatively close object at the retina 22. Note that if the lens could not accommodate, the image of the relatively close object would be located behind the retina, and would appear blurred.

Figure 4:
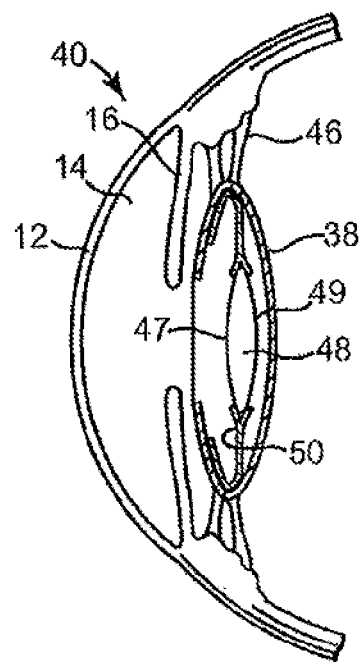
FIG. 4 is a plan drawing of the human eye of FIG. 3, in an accommodative "far" state.

FIG. 4 shows a portion of an eye 40 that is focused on a relatively distant object. The cornea 12 and anterior chamber 14 are typically unaffected by accommodation, and are identical to the corresponding elements in FIG. 3. To focus on the distant object, the zonules 46 retract and change the shape of the capsular bag 38, which becomes thinner at its center and has less steeply curved sides. This reduces the lens power by flattening (e.g., lengthening radii of curvature and/or thinning) the lens, placing the image of the relatively distant object at the retina (not shown).

For embodiments as depicted for both the "near" case of FIG. 3 and the "far" case of FIG. 4, the intraocular lens itself deforms and changes in response to the distortion of the capsular bag. For the "near" object, the haptic 30 compresses the optic 28 at its edge, increasing the thickness of the optic 28 at its center and more steeply curving its anterior face 27 and/or its posterior face 29. As a result, the lens power increases. For the "far" object, the haptic 50 expands, pulling on the optic 48 at its edge, and thereby decreasing the thickness of the optic 48 at its center and less steeply curving (e.g., lengthening one or both radius of curvature) its anterior face 47 and/or its posterior face 49. As a result, the lens power decreases.

Note that the specific degrees of change in curvature of the anterior and posterior faces depend on the nominal curvatures. Although the optics 28 and 48 are drawn as bi-convex, they may also be plano-convex, meniscus or other lens shapes. In all of these cases, the optic is compressed or expanded by essentially radial forces exerted primarily at the edge of the optic. In addition, there may be some axial movement of the optic. In some embodiments, the haptic is configured to transfer the generally symmetric radial forces symmetrically to the optic to deform the optic in a spherically symmetric way. However, in alternate embodiments the haptic is configured non-uniformally (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optics may optionally have one or more diffractive elements, one or more multifocal elements, and/or one or more aspheric elements.

Figure 5:
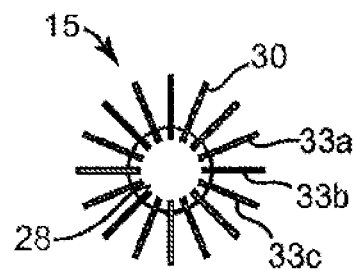
FIG. 5 is an end-on plan drawing of the intraocular lens shown in FIGS. 3 and 4, in an accommodative "near" state.
Figure 6:
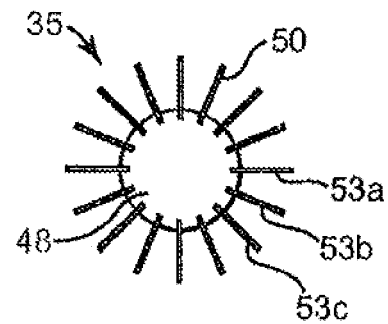
FIG. 6 is an end-on plan drawing of the intraocular lens of FIG. 5, in an accommodative "far" state.

FIGS. 5 and 6 show more explicitly the effects of these radial forces. FIG. 5 shows the intraocular lens 15 of FIG.

3, in an end-on view. The optic 28 is supported by the haptic 30. The intraocular lens 15 is relatively compressed radially, corresponding to the "near" condition of FIG. 3. Similarly, FIG. 6 shows the intraocular lens 35 of FIG. 4 in an end-on view, also with the optic 48 being surrounded by the haptic 50. Here, the intraocular lens 35 is relatively expanded radially, corresponding to the "far" condition of FIG. 4.

Each haptic 30 and 50 can have several coupling elements 33 and 53. Each coupling element is substantially free to move radially, independently of the other coupling elements. As the capsular bag expands and contracts, the coupling elements transmit the expansion and contraction to the optic itself, causing the optic to expand or contract radially. When the eye views a distant object, the radial forces cause the optic itself to be flatter and thinner than when viewing a close object. In some embodiments, there may also be some axial movement of the optic, which axially translates the image onto the retina and thereby brings it into focus for the eye. Any such axial travel will typically be of secondary importance to the change in power caused by the shape change to the optic caused by the radial forces. The haptic material is preferably stronger or stiffer than the optic material, so that the capsular bag force is largely transmitted to the optic itself, rather than being absorbed by the haptic. Although 16 coupling elements are shown in FIGS. 5 and 6, any suitable number of haptic elements may be used.

Note also that as drawn in FIGS. 3-6, in some embodiments, there is no haptic material between adjacent coupling elements. If there were a substantial amount of haptic material between the coupling elements, the radial force would be largely absorbed by the haptic, rather than transmitted to the optic. Alternatively, there may be some haptic material between adjacent coupling elements, provided that it is relatively thin if it is made from the same stiff or strong material as the coupling elements. A thin membrane or coating of haptic material between the coupling elements would work adequately, and would not impede any diametric or radial motion of the optic. The membrane could be located symmetrically or asymmetrically along the longitudinal axis of the lens; the haptic may have an even distribution along the longitudinal axis of the optic, or may have more material near the anterior side of the optic, for instance, or may have more material near the posterior side of the optic. Alternately, the membrane may be made in one piece with the coupling elements and may be located anywhere along the coupling elements (e.g., attached to the optic or not so attached, on either end of the coupling elements or somewhere in the middle of the coupling elements). Alternatively, the membrane may be made thicker if it is made from a softer material than that used for the haptic. In general, a thin membrane would function adequately if it is circumferentially compressible, e.g., if its size or circumference can increase or decrease without buckling, warping, or crumpling. For the purposes of this document, the terms circumferentially compressible and circumferentially expandable are taken to mean the same thing.

As a further alternative, the thickness of the material between coupling elements may be increased if said material is weaker or less stiff than the material of the coupling elements themselves. This material may be useful in distributing the haptic force more uniformly around the circumference of the optic. Ultimately, any suitable haptic design may be used, provided that the haptic permits diametric or radial alteration (e.g., change of shape in response to radial or diametric force from the haptic) of the optic in response to the contraction or expansion of the capsular bag.

Note that in FIG. 3, the optic 28 is spatially separated from the posterior wall 20 of the capsular bag 18. In this case, the optic 28 distorts in response to the radial forces applied to its edge by the haptic 30, rather than in response to any longitudinal (or, equivalently, axial) forces applied to the anterior face 27 or posterior face 29. As an alternative, the optic 28 may come into contact with the posterior wall 20 of the capsular bag 18 during part or all of the accommodation range, and in doing so, may receive some longitudinal forces applied to its posterior face 29.

In. FIG. 3, the haptic 30 interacts with thin portions of the optic near the edge of the anterior face 27 and the posterior face 29 of the optic. For the purposes of this document, these interactions may be considered to be with the edge of the optic if the forces exerted by the haptic on the optic are essentially radial in nature, and if the thin portions are outside the clear aperture of the optic. Note that in FIGS. 3 and 4, the entire edge of the optic, from anterior to posterior, is contacted by the haptic. Note also that for the purposes of this document, the edge of the optic is intended to mean the peripheral edge of the optic, which is the outermost edge of the optic that connects the anterior and posterior faces of the optic. The edge may be a surface periphery as well.

Figures 7, 8:
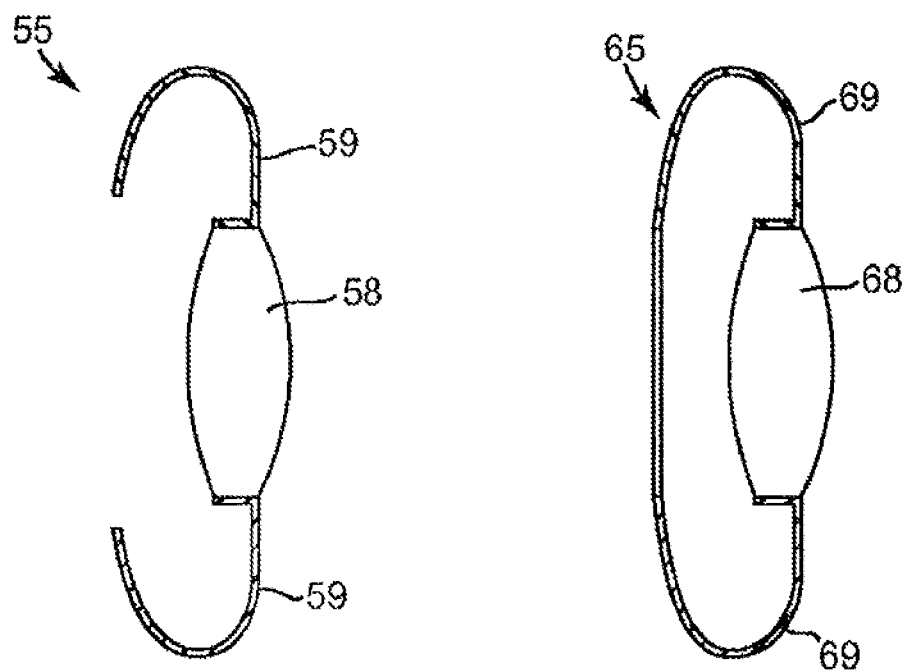
FIG. 7 is a cross-sectional drawing of an intraocular lens that can have electronics or other features as disclosed herein according to some embodiments of the invention.
FIG. 8 is a cross-sectional drawing of another embodiment of an intraocular lens that can have electronics or other features as disclosed herein according to some embodiments of the invention.

FIG. 7 shows an alternate embodiment of an intraocular lens 55. The lens has an optic 58, which is mechanically coupled to the capsular bag by a haptic 59. Alternately, the haptic may actually be connected to the capsular bag by fibrosis or surface treatments. As with the embodiments of FIGS. 3-6, the haptic 59 may have several coupling elements or filaments, each of which couples the capsular bag radial force into the optic 58 itself. As a result, the haptic permits diametric expansion and contraction of the optic 58.

Unlike the embodiments of FIGS. 3-6, in which the haptic has an engagement member with a central recess that receives the peripheral edge of the optic, the haptic 59 could have a planar member that interacts only with the edge of the optic 58. Note that the haptic 59 extends from substantially the entire edge of the optic 58. It will be understood by one of ordinary skill in the art that various other configurations may be used to form an interaction between the haptic and substantially the entire edge of the optic. Alternatively, the haptic could extend over only a portion (either axially or circumferentially) of the edge of the optic, having asymmetries, discontinuities, and/or a bias toward one side or the other.

Note that the haptic may optionally convert the capsular bag force to a radial torque, rather than transmit the force itself to the optic. The equator of the optic may be axially separated from the region at which the capsular bag force is applied, thereby generating a torque. Such a torque affects the optic by changing its shape and/or axially translating the optic.

In some embodiments, the coupling elements may all be connected on the anterior side of the haptic 69. Because it can, in some cases be undesirable to block the clear aperture of the optic, the anterior side of the haptic may join the coupling elements in a ring 62 surrounding the clear aperture.

Figure 9:
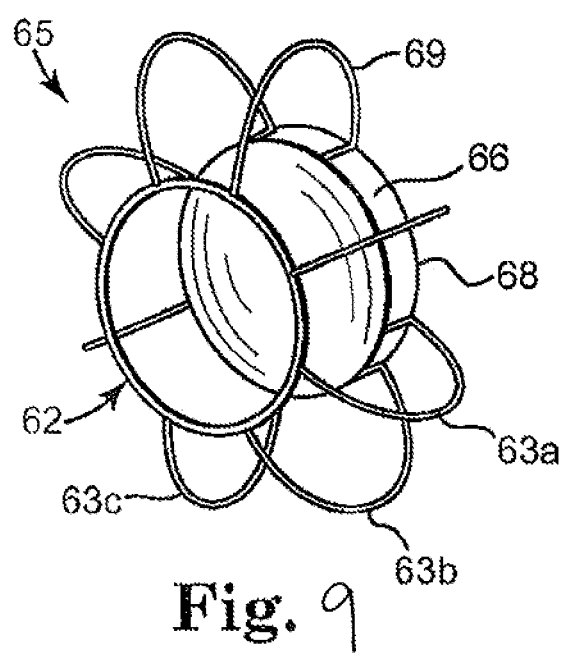
FIG. 9 is a perspective drawing of the intraocular lens of FIG. 6.

Note that in the intraocular lens 65 of FIGS. 8 and 9, a fairly rigid ring 62 joining the coupling elements is acceptable, because it does not surround the optic 68 and it does not impede any radial or diametric motion of the optic. Here, the capsular bag radial force is still directed into radially compressing or expanding the optic 68, only now it does it through a lever arm, with the fixed point on the lever being the anterior ring that joins the coupling elements. Alternately, the coupling elements may connected by a broken ring that connects only some of the coupling elements.

FIG. 9 shows the haptic 69 connected to the optic 68, with an optional membrane 66 between the coupling elements 63. The membrane 66 may be connected to the optic 68 everywhere between the coupling elements 63, or may be connected only in portions, or may be not connected at all in the regions between the coupling elements 63. The membrane 66 may optionally be located between the coupling elements 63 and the optic 68 at each element's connection point, or may be located in only the regions between adjacent coupling elements 63. The membrane may be made as a single piece with the haptic or as a separate element. The membrane 66 may be made of the same material as the haptic 69, with a small enough thickness so that it does not impede any radial expansion or compression of the optic 68 during accommodation. Alternatively, the membrane 66 may be made of a different (typically softer) material than the haptic 69. All of these embodiments could be applied equally to an embodiment as shown in FIG. 7 that does not have the ring 62.

In the embodiments of FIGS. 3-9, the optic can be oriented on the posterior side of the capsular bag. The preference for a posterior optic is based on a number of factors, including, for example: avoidance or limitation of retinal detachment, which is often more likely with anterior optics; avoidance of iris or anterior chamber complications; and prevention or limitation of posterior capsule opacification. Alternatively, the optic may be oriented on the anterior side of the capsular bag, with the optional connecting ring located on the posterior side of the haptic.

As a further alternative, two or more optics may be used, with one on the anterior side and one on the posterior side of the haptic. As the capsular bag expands or contracts, the haptic expands or contracts both optics simultaneously. If one optic is stiffer than the other, it could act effectively as the fixed point on a lever arm, similar to the ring 62 in FIG. 9. Optionally, the separation between the two optics may vary as well.

It is instructive to discuss the properties of some suitable materials for the haptic and the optic. In general, the optic should be a fairly soft material, so that it can deform sufficiently under the limited force of the zonules. In general, the haptic should be a fairly hard or stiff material, so that the force from the zonules is transmitted efficiently to the optic. A useful quantity for comparison is the Young's modulus of the materials. For the optic, a low Young's modulus is preferred, such as a value of 28 kpa or less. For the haptic, a high Young's modulus is preferred, such as 1000 kpa or more. Typical haptic materials include, but are not limited to, silicone, acrylic, polyimide, PMMA, polyurethane or other biocompatible materials. Typical optic materials include, but are not limited to, silicone, acrylic, PMMA, and various suitable hydrogels.

The optic itself may be solid throughout, or may be a balloon structure. The optic may be generally soft throughout, or may have a thin, stiff layer on top of a soft structure. The optic may also be a multilayer structure, or may contain multilayered elements.

The haptic may be made integral with the optic. For instance, the two may be molded together. Alternatively, they may be manufactured separately and assembled. Some common assembly methods are silicone glue or adhesive, ultraviolet light-cured adhesive, or heat-cured adhesive.

Note that the haptic can be, in some embodiments, generally a filament in nature, which is a fine or thinly spun thread, fiber, or wire. This filamentary shape minimizes the mass of the haptic. Because the force that can be applied by the capsular bag is limited, and responsiveness to this force is highly desirable, it is also desirable to minimize the mass of the haptic so that the eye can accommodate quickly. A light haptic tends to speed up the response of the eye, which is desirable. The haptic filaments (e.g., coupling elements) have essentially the same size at each point along their length, so that the cross-section of each filament remains essentially uniform along its length. The filaments that form the coupling elements of the various embodiments described above will typically have two ends, one of which is coupled to the optic, with a coupling portion between the two ends for engaging the capsular bag and/or zonules. Note that the connecting ring may optionally have a different thickness than the filaments, and that one or more filaments may have different thicknesses than other filaments. One or more of the filaments may be shaped to produce a bending in a particular manner, as with a pre-bent or a memory-retaining material.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting an intraocular lens into the anterior chamber" include "instructing the inserting of an intraocular lens into the anterior chamber." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers, and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. An implantable intraocular lens (IOL), comprising:
an optic;
a haptic attached to the optic;
a forward-facing camera on the haptic;

a power source on the haptic;

a display on the optic, the display sized and configured to overlay graphics in the user's view of the physical world;

a processor on the haptic configured to receive signals from the camera and send graphics data to the display;

a communications module on the haptic, the communications module configured to wirelessly transmit and receive information with respect to an external device.

2. The implantable intraocular lens of claim 1, wherein the lens is a pseudophakic lens.

3. The implantable intraocular lens of claim 1, wherein the lens is an accommodating lens.

4. The implantable intraocular lens of claim 1, wherein the lens is a phakic lens.

5. The implantable intraocular lens of claim 1, comprising a plurality of optics.

6. The implantable intraocular lens of claim 1, wherein the camera comprises a video camera.

7. The implantable intraocular lens of claim 1, wherein the display comprises LED technology.

8. The implantable intraocular lens of claim 1, wherein the display is centered on the optic.

9. The implantable intraocular lens of claim 1, wherein the display is off-centered on the optic.

10. The implantable intraocular lens of claim 1, further comprising a GPS chip.

11. The implantable intraocular lens of claim 1, further comprising a RFID chip.

12. The implantable intraocular lens of claim 1, wherein the communications module comprises cellular technology.

13. The implantable intraocular lens of claim 1, wherein the communications module comprises 802.11 technology.

14. The implantable intraocular lens of claim 1, wherein the power source is wirelessly rechargeable via an external source.

\* \* \* \* \*